United States Patent [19]

Barbuto

[11] 4,325,365
[45] Apr. 20, 1982

[54] ATHLETE'S BREATHING APPARATUS

[76] Inventor: John P. Barbuto, 5801 S. 300 East #260, Murray, Utah 84107

[21] Appl. No.: 215,190

[22] Filed: Dec. 11, 1980

[51] Int. Cl.$^3$ ............................................. A62B 7/00
[52] U.S. Cl. ........................... 128/201.13; 128/204.17
[58] Field of Search ....................... 128/201.13, 204.17

[56] References Cited

U.S. PATENT DOCUMENTS

| 3,326,214 | 6/1967 | McCoy | 128/201.13 |
| 4,196,728 | 4/1980 | Granite | 128/201.13 |

FOREIGN PATENT DOCUMENTS

| 1364599 | 5/1964 | France | 128/202.13 |
| 23279 | of 1894 | United Kingdom | 128/201.13 |

Primary Examiner—Henry J. Recla
Attorney, Agent, or Firm—K. S. Cornaby

[57] ABSTRACT

A breathing apparatus for athletes to warm and moisturize inhaled air has an elongate housing having both lateral and downward curvatures with respect to the position of the apparatus when positioned over the mouth of the wearer. An oral aperture for disposition over the mouth of the wearer is disposed centrally of the housing on the concave side of the lateral curvature. A plurality of corresponding pairs of spaced-apart leaf members or vanes disposed within the housing. The leaf members are disposed so that the inner ends of the pairs of members form a chamber adjacent to the oral aperture, with the chamber having diminishing depth from front to rear so as to permit the leaf member ends to catch and distribute exhaled air along passages formed by the leaf members. The exhaled air warms and moisturizes the leaf members, which in turn warm and moisturize the inspired air to prevent damage to sensitive tracheal membranes of runners in cold weather.

6 Claims, 3 Drawing Figures

ATHLETE'S BREATHING APPARATUS

BACKGROUND OF THE INVENTION

This invention relates to apparatus for aiding athletes, particularly runner, to warm inspired air in cold environments to prevent cold air damage to tracheas.

In recent years, increased attention has been given to physical exercise as a means of promoting and maintaining good health. Running or jogging in the outdoors environment is emerging as one of the most popular forms of physical exercise, since it is available to virtually everyone and requires no particular equipment or physical facilities. As the popularity of running has increased, runners and their physicians have become more aware of a respiratory problem that can arise when runners run during cold weather. The problem is known as "burned trachea" caused by large amounts of very cold air being inspired by runners and causing extreme discomfort or damage to the delicate membranes of the trachea. The solution to the problem has been viewed as finding a means for providing warmed air for inspiration in a manner which will not hinder or encumber the runner.

Various breathing devices for medical purposes have long been known. Devices such as those disclosed in U.S. Pat. Nos. 2,610,038; 2,784,714; 3,333,585; 3,490,477; 3,707,966; 3,747,598; 4,136,691; and 4,150,671 have been developed for the purpose of heating inspired air and/or introducing medicaments into the air stream. Bulky size, inefficient design and reduced air flow have made these devices impractical for use by runners and joggers.

Attempts to develop more efficient or lighter weight alternative devices, such as disclosed in U.S. Pat. Nos. 3,326,214 and 3,814,094 respectively, have neither addressed nor solved the unique problem facing cold weather runners. Such runners require a breathing device which is highly efficient in heat and moisture exchange, light weight, minimally restrictive of air flow, leaving the nasal passages unobstructed, and providing means for rapid dissipation of collected moisture.

It is an object of the present invention to provide a portable heat-exchange breathing apparatus for runners and joggers, which will warm cold air, partially remoisturize inspired air and provide rapid dissipation of unusable moisture condensing from the expired air.

It is further object of the present invention to provide an apparatus for use orally only which is light-weight, highly efficient and has high air flow capabilities, and which will minimize the possibility of inflicting to the face or mouth of a runner in case of an accident.

BRIEF SUMMARY OF THE INVENTION

According to the invention, a portable breathing apparatus for athletes to warm cold inspired air and remove unwanted moisture condensation has a housing adapted to cover the mouth of the wearer's head. The housing is curved both downwardly and rearwardly to fit around the wearer's mouth and head. A plurality of closely-spaced corresponding pairs of leaf members preferably constructed of a rapid heat-exchanging metal, are disposed within the housing preferably in parallel relationship with each other and with each member of a pair extending laterally outwardly from the center of the housing.

The housing has an aperture in the center of the concave side thereof corresponding to the location of the mouth of the wearer. The pairs of laterally-extending leaf members are disposed within the housing so as to functionally subdivide the column of air as it is expired from the mouth into the central aperture in the housing.

The lateral side or ends of the housing are open to permit maximum air flow into and from the housing, while the downward curve of the housing permits moisture condensation to drain rapidly away from the center of the housing and fall from the open ends of the housing.

DRAWING

A preferred embodiment of the invention is illustrated in the attached drawing, in which.

DETAILED DESCRIPTION OF THE ILLUSTRATED EMBODIMENT

Figure 1:
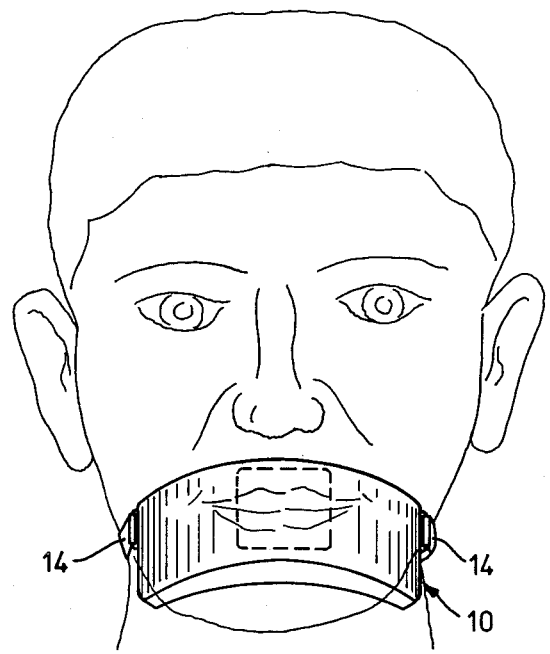
FIG. 1 is a front elevational view of the apparatus shown in place on the face of a wearer.
Figure 2:
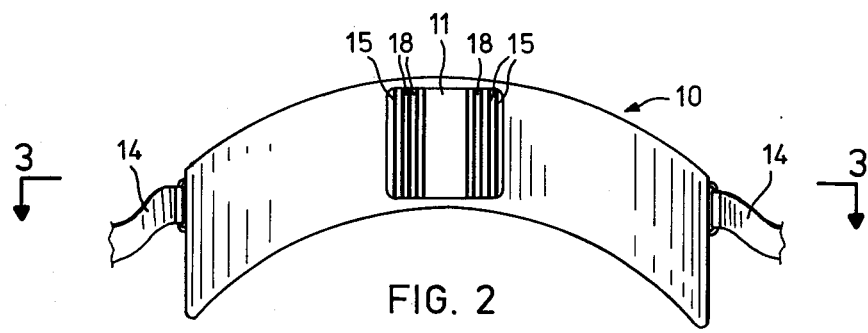
FIG. 2 is a side elevational view of the apparatus showing the oral aperture for disposition head to the face.
Figure 3:
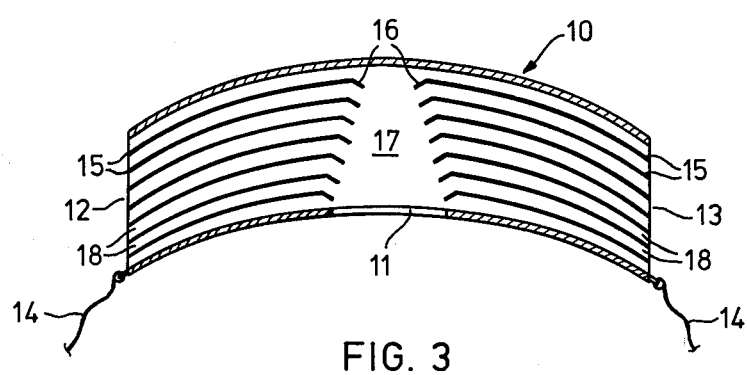
FIG. 3 is a top plan sectional view of the apparatus taken along line 3—3 of FIG. 2.

As shown in FIGS. 1, 2, and 3, a preferred embodiment of the invention has a housing 10 which is adapted to fit around the contour of a wearer's face (shown in outline form in FIG. 1). Housing 10 is curved in two directions with respect to its position on the wearer's face; i.e., both downwardly and rearwardly around the face, and has an oral aperture 11, shown in FIG. 2, for disposition next to the wearer's mouth, and respective apertures 12, 13 on both ends of housing 10, essentially providing that both ends of housing 10 are open to the atmosphere. It is important to the proper functioning of the apparatus that housing 10 have both rearward and downward curvatures. The rearward curvature accomodates the contour of the wearer's face, so that a snug, close-fitting position around the wearer's mouth is attained. This configuration permits the wearer to breathe through his mouth while running and insure that the experation is channeled into aperture 11 and inhalation is accomplished through the same aperture. If the wearer desires to inspire cold air directly, the wearer's nose is not covered at any time and can be used to regulate the amount and approximate temperature of the inspired air. In fact, it is preferable to exclude the nose since the physiology of the nose has been adapted to specifically perform the functions of heat and moisture exchange at low volumes. It is only when the repiratory rates exceed the nasal capabilities that a similar function for the mouth must be provided. To cover the nose decreases the efficiency of the system, since the nose already is maximally efficient within its limitations.

The downward curvature of the housing 10 couple with aperture 12, 13 permits rapid drainage of moisture condensation from housing 10 so as not to interfere with the free flow of air through the apparatus.

Housing 10 is preferably constructed of light weight material, such as plastic or the like which is impervious to moisture and is not adversely affected by cold temperatures. Housing 10 should be constructed of material which will not fragment upon being struck, so that in the event of a fall a runner would not be likely to experience facial lacerations.

Means for attaching housing 10 to a wearer's head as illustrated in FIG. 1, is acomplished in this embodiment by a plurality of straps 14, which a preferably adjustable and of a stretchable material to provide a snug, comfortable fit around the wearer's head.

Housing 10 contains a plurality of spaced-apart leaf members 15 disposed in parallel relationship to each other and extending laterally outwardly from the center of housing 10 to the end apertures 12, 13 thereof. Leaf members 15 are preferably constructed of a rapidly heat-exchanging metal, such as thin-leaf copper, aluminum or the like. Leaf members 15 are very thin and have smooth surfaces so as not to impede the flow of air. Members 15 are spaced closely together in parallel relationship, preferably the order of 0.3 cm. between each leaf.

It is of importance that leaf members 15, are so disposed that they functionally subdivide the column of expired air from the mouth. This is accomplished by arranging the corresponding pairs of oppositely disposed leaf pairs so that the inner ends 16 of the leaf members form a chamber 17 of diminishing width as shown in FIG. 3. Ends 16 are preferably angled forwardly toward aperture 11 to deflect a portion of the exhaled air into the laterally-extending air passages 18 between adjacent leaf members 15. This unique configuration of leaf members 15 provides for rapid and relatively even dispersal of exhaled air through the apparatus, so that warm exhaled air heats and moisturizes leaf members 15 which, in turn, provide heat and moisture for incoming inspired cold air to be heated and moisturized before reaching the sensitive tracheal tissues. The objective of high air-flow, high efficiency, heat exchange, and uniform air flow past all leaf members 15 is thereby achieved.

While this invention has been illustrated and described with respect to a preferred embodiment, it should be understood that substantial equivalents are contemplated as coming within the scope of the invention, which is defined by the appended claims.

I claim:

1. An apparatus for warming and moisturizing inspired cold air for athletes, comprising in combination:

A hollow housing having both a downward and a lateral curvature for fitting over the mouth of a wearer; said housing having an oral aperture disposed centrally of the laterally curving portion of said housing on the concave side thereof; said housing also having mutually opposing open lateral ends;

Strap means attached to said housing for securing said housing to the head of a wearer; and A plurality of mutually spaced-apart analogous pairs of leaf members with each member of a pair extending laterally within said housing outwardly from the center to said ends of said housing; said pairs of leaf members being arranged with in said housing so that a chamber is formed next to said oral aperture by the inner ends of said leaf members, said chamber having diminishing width created by decreasing distance between the ends of successive leaf pairs from the oral aperture to the opposite side of said housing.

2. A breathing apparatus as set forth in claim 1, wherein said inner ends of said plurality of leaf members are angled inwardly toward said oral aperture in the housing.

3. A breathing apparatus as set forth in claim 1, wherein said leaf members are constructed of a material having a high heat exchange capability.

4. A breathing apparatus as set forth in claim 3, wherein said leaf members are constructed of copper.

5. A breathing apparatus as set forth in claim 3, wherein said leaf members are constructed of aluminum.

6. A breathing apparatus as set forth in claim 1, wherein said housing is constructed of plastic material.

* * * * *